(12) United States Patent
Madani et al.

(10) Patent No.: US 10,679,345 B2
(45) Date of Patent: Jun. 9, 2020

(54) AUTOMATIC CONTOUR ANNOTATION OF MEDICAL IMAGES BASED ON CORRELATIONS WITH MEDICAL REPORTS

(71) Applicant: International Business Machines Corporation, Armonk, NY (US)

(72) Inventors: Ali Madani, Oakland, CA (US); Mehdi Moradi, San Jose, CA (US); Tanveer F. Syeda-Mahmood, Cupertino, CA (US)

(73) Assignee: International Business Machines Corporation, Armonk, NY (US)

(*) Notice: Subject to any disclaimer, the term of this patent is extended or adjusted under 35 U.S.C. 154(b) by 15 days.

(21) Appl. No.: 15/848,777

(22) Filed: Dec. 20, 2017

(65) Prior Publication Data
US 2019/0188848 A1 Jun. 20, 2019

(51) Int. Cl.
*G06K 9/00* (2006.01)
*G06T 7/00* (2017.01)
(Continued)

(52) U.S. Cl.
CPC .......... *G06T 7/0012* (2013.01); *A61B 6/5229* (2013.01); *G06N 3/0445* (2013.01); *G06N 3/0454* (2013.01); *G06N 3/08* (2013.01); *G16H 10/40* (2018.01); *G16H 10/60* (2018.01); *G06T 2207/30004* (2013.01)

(58) Field of Classification Search
CPC ........ G06T 7/0012; G06T 2207/30004; G16H 10/40; G16H 10/60; A61B 6/5229
See application file for complete search history.

(56) References Cited

U.S. PATENT DOCUMENTS 10,140,421 B1 * 11/2018 Bernard ................ G06F 19/321
2013/0226843 A1 8/2013 Syeda-Mahmood et al.
(Continued)

OTHER PUBLICATIONS

High, Rob, "The Era of Cognitive Systems: An Inside Look at IBM Watson and How it Works", IBM Corporation, Redbooks, Dec. 12, 2012, 16 pages.
(Continued)

*Primary Examiner* — Xin Jia
(74) *Attorney, Agent, or Firm* — Stephen J. Walder, Jr.; William J. Stock (57) ABSTRACT

Mechanisms are provided to implement a neural network, a concept extractor, and a machine learning model that operate to provide automatic contour annotation of medical images based on correlations with medical reports. The neural network processes a medical image to extract image features of the medical image. The concept extractor processes a portion of text associated with the medical image to extract concepts associated with the portion of text. The machine learning model correlates the extracted image features with the extracted concepts. An annotated medical image is generated based on the correlation of the extracted image features and extracted concepts. An annotation of the annotated medical image specifies a region of interest corresponding to both an extracted image feature and an extracted concept, thereby automatically mapping the portion of text to a relevant region of the medical image.

20 Claims, 5 Drawing Sheets

(51) Int. Cl.
*A61B 6/00* (2006.01)
*G16H 10/40* (2018.01)
*G16H 10/60* (2018.01)
*G06N 3/04* (2006.01)
*G06N 3/08* (2006.01)

(56) References Cited

U.S. PATENT DOCUMENTS

2015/0065803 A1* 3/2015 Douglas ............. A61B 1/00009
                                                    600/200
2018/0060512 A1* 3/2018 Sorenson .............. G06T 7/0012
2018/0166167 A1* 6/2018 Kanada .................. G06Q 50/22

OTHER PUBLICATIONS

Moradi, Mehdi et al., "A Hybrid Learning Approach for Semantic Labeling of Cardiac CT Slices and Recognition of Body Position", 2016 IEEE 13th International Symposium on Biomedical Imaging (ISBI), Apr. 13-16, 2016, pp. 1418-1421.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

* cited by examiner

AUTOMATIC CONTOUR ANNOTATION OF MEDICAL IMAGES BASED ON CORRELATIONS WITH MEDICAL REPORTS

BACKGROUND

The present application relates generally to an improved data processing apparatus and method and more specifically to mechanisms for providing automatic contour annotation of medical images based on correlations with medical reports.

Medical images, especially labeled (or annotated) images, are difficult and expensive to acquire. Often such labeled images require large expenditures of human effort and resources where a human subject matter expert (SME) must manually identify anatomical structures and characteristics within the medical images and annotate the medical images with identifiers of such anatomical structures and characteristics.

Machine learning algorithms may be trained to classify different medical conditions in medical imaging, such as identifying medical images with anomalies or diseases present in the medical images, and differentiating such medical images showing anomalies and diseases from normal medical images in which such anomalies are present. Such training often requires large sets of annotated or labeled medical images in order for the machine learning algorithm to reach convergence. Unfortunately, however, most sources of medical images provide the medical images as unlabeled or non-annotated medical images.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, wherein the at least one memory comprises instructions that are executed by the at least one processor to cause the at least one processor to implement a neural network, a concept extractor, and a machine learning model. The method comprises processing, by the neural network of the data processing system, a medical image to extract image features of the medical image, and processing, by the concept extractor of the data processing system, a portion of text associated with the medical image to extract concepts associated with the portion of text. The method further comprises correlating, by the machine learning model of the data processing system, the extracted image features with the extracted concepts. Moreover, the method comprises generating, by the data processing system, an annotated medical image based on the correlation of the extracted image features and extracted concepts. An annotation of the annotated medical image specifies a region of interest corresponding to both an extracted image feature and an extracted concept, thereby automatically mapping the portion of text to a relevant region of the medical image.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

As noted above, most sources of medical images provide the medical images as unlabeled or non-annotated medical images. For example, many hospitals, medical imaging laboratories, medical imaging service providers, and the like, are able to provide the medical images in a digital format, but the medical images are provided in a raw unlabeled form. However, it has been recognized that such medical images are often available with associated medical report documents that reference findings in the medical images, e.g., whether the medical image is normal or shows an abnormality, measurements of abnormalities, locations of abnormalities, and the like. The illustrative embodiments described herein recognize that these medical report documents can provide information on where abnormalities exist within the accompanying medical image and the characteristics of the abnormality, even though the abnormality may not be specifically labeled or annotated in the medical image data itself.

The illustrative embodiments provide mechanisms for providing automatic contour annotation of medical images based on correlations with medical reports. The illustrative embodiments provide mechanisms for concatenating features extracted from a medical image with concepts extracted from an accompanying or associated electronic medical report document to identify a region in the medical image where an anomaly is detected. Based on the concatenation of the extracted features of the medical image and the concepts extracted from the accompanying medical report document, the illustrative embodiments provide automatic contouring of abnormalities in the medical image. The automatic contouring converts the medical image into an annotated or labeled medical image which may then be used to train a cognitive system, machine learning algorithm, convolutional neural network, or other artificial intelligence mechanism that may be used to perform medical image classification and/or other cognitive operations. Such automatic contouring based on the associated electronic medical report document allows for faster and more efficient annotation of medical images than using manual annotation or labeling techniques as are generally utilized.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for providing automatic contour annotation of medical images based on correlations with medical reports. With the mechanisms of the illustrative embodiments, an electronic medical report document (hereafter referred to as a "medical report") associated with a medical image, or set of medical images, such as a medical imaging study, is input to a concept extractor to isolate key terms, phrases, descriptors, and other natural language content elements that references features of a medical image. The natural language processing performed by the concept extractor may be specifically configured for analysis of text with regard to medical imaging concepts and features of medical images. The natural language content elements, e.g., words, may then be embedded in a vector space. In one illustrative embodiment, the vector space is a glove vector space, where a glove is an unsupervised learning algorithm for obtaining vector representations for words. Training is performed on aggregated global word-word co-occurrence statistics from a corpus, and the resulting representations showcase interesting linear substructures of the word vector space.

The series of vectors in the vector space are then fed-forward through a long short-term memory (LSTM) network which processes semantic and relational information in sentences. A long short-term memory (LSTM) network is a recurrent neural network (RNN) architecture that remembers values over arbitrary intervals.

In addition, the associated medical image may be processed by a convolutional neural network (CNN) which extracts features from the medical image and provides a vector output representing these extracted features. The processing of the medical image may be done in parallel to the processing of the medical report through the LSTM network.

The features from the CNN are concatenated with the output of the LSTM network and sent through a multi-layer perceptron (MLP). In machine learning, the perceptron is an algorithm for supervised learning of binary classifiers, i.e. functions that can decide whether an input (represented by a vector of numbers) belongs to one class or another. The perceptron is a type of linear classifier, i.e. a classification algorithm that makes its predictions based on a linear predictor function combining a set of weights with the feature vector. The final output layer of the multi-layer perceptron is a series of points for the contour of one or more abnormalities that is regressed using a mean squared error loss function.

The CNN in the illustrative embodiments operates as a descriptor generation engine and generates numerical values that are a descriptor of the medical image and which are represented as a vector output. The LSTM network receives textual data as an input from the medical report and converts the textual data input into a vector (vector embedding). Thus, the CNN provides a vector output representative of the medical image features and the LSTM network provides a vector output representative of the key terms, phrases, or other natural language content elements (hereafter assumed to be words for purposes of illustration).

A machine learning model, e.g., a multi-layer perceptron (MLP) in some illustrative embodiments, is trained on these vector outputs together. For example, the training may involve inputting to the machine learning model, an input training medical image dataset where it is known, for each medical image in the dataset, what the coordinates are of the bounding region of where an abnormality exists within the input training medical image dataset, and where there is electronic textual data associated with the medical image, such as in an electronic medical report document accompanying or associated with the training medical image. For example, the medical image data for a medical image in the training medical image dataset may have metadata identifying the four vertex points of a polygonal region where an abnormality is present in the medical image, although other coordinates of more or less points of a bounding region (contour) of various configurations may be used depending on the desired implementation. The associated electronic text identifies medical concepts of abnormalities.

Through training, the vector representation of the medical images in the training medical image dataset and the vector representation of the associated electronic text is used to identify relationships between the two such that when similar text is found in other electronic text, e.g., electronic medical report documents, associated with other medical image data, similar regions of those medical images may be identified and annotated. Thus, for example, assume that there may be 256 numerical values in an output vector that describes a medical image and 256 numerical values that describe text. The machine learning model concatenates these and is trained to output the coordinates of points along a bounding region, e.g., 4 vertex points of a polygon, of a contour indicating a region where the abnormality specified in the text lies in the medical image.

Figure 1:
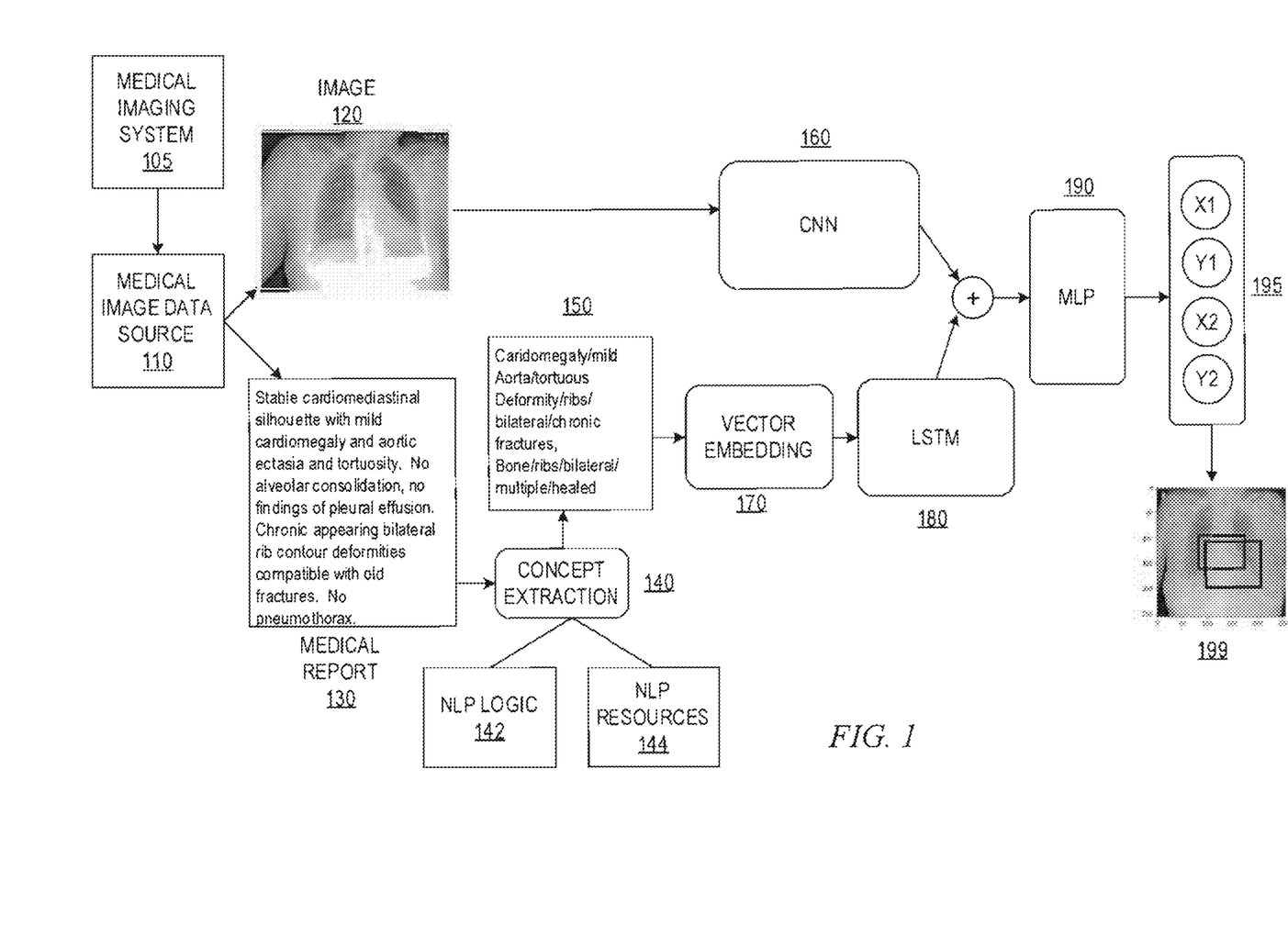
FIG. 1 is an example block diagram of a data flow in accordance with one illustrative embodiment.

FIG. 1 is an example block diagram of a data flow in accordance with one illustrative embodiment. As shown in FIG. 1, a medical image data source 110 provides a medical image dataset 120 and corresponding medical report data structure 130. The medical image data source 110 may be any computer system that collects and stores medical image data from one or more imaging systems 105 of the same or various types. For example, the one or more imaging systems 105 may comprise medical imaging equipment that performs medical imaging on patients using X-ray imaging, CT scan imaging, MM imaging, sonogram imaging, and/or the like. The images captured by the one or more imaging systems 105 of a patient are rendered as a digital representation which is stored in the medical image data source 110 as a medical image dataset 120. The medical image dataset 120 may comprise a single, or multiple medical images, where in the case of multiple medical images, the medical images may be taken with different viewpoints. For ease of depiction, FIG. 1 shows the medial image dataset 120 as a single medical image of a chest X-ray, however it should be appreciated that the dataset 120 may comprise a plurality of medical images, such as may be provided as part of a medical imaging study, and the medical image dataset 120 may use other imaging technologies and modalities of other regions of a biological entity (whether human, animal, or plant) other than that of a chest X-ray.

A human subject matter expert (SME), such as radiologist, sonographer, or the like, may view the medical image(s) of the medical image dataset 120 and generate an electronic medical report document 130 detailing the SME's findings in the medical image. The electronic medical report document 130 may be generated via textual input from the SME, via a voice recording with speech-to-text translation, or the like. The electronic medical report document 130 comprises terms, phrases, and the like, that describe medical concepts represented in the corresponding medical image 120, e.g., anomalies, diseases, etc., and/or specific references to features or portions of the medical image 120.

The electronic medical report document 130 is input to a concept extractor 140. The concept extractor 140 may comprise natural language processing (NLP) logic 142 which operates on the electronic medical report document 130 to extract key terms, phrases, concepts, and other descriptors that are present in the electronic medical report document 130 that are indicative of references to medical concepts and/or features of the medical image 120. The NLP logic 142 may utilize various NLP resources 144 to assist with identification of such key terms, phrases, concepts and other descriptors, such as dictionary data structures, synonym data structures, domain specific knowledge bases, and the like. For example, the NLP resources 144 may be specifically configured for the particular domain of medical images being analyzed. In some illustrative embodiments, when the medical image dataset 120 is received, metadata associated with the medical image dataset 120 and/or the associated medical report document 130 may be utilized to identify characteristics of the medical image dataset 120 including, for example, the domain of the medical image (e.g., anatomical region of the biological entity), the medical image technology utilized, the modality, etc. For example, the metadata may specify that the medical image dataset 120 is for medical images of the chest and the imaging technology utilized is an X-ray. Based on this information, the NLP logic 142 may retrieve and utilize resources from the NLP resources 144 that correspond to the particular domain and imaging technology, e.g., particular key terms, phrases, concepts, and descriptors associated with anomalies and diseases typically present in the anatomical region of the chest, and which are identifiable by X-ray imaging.

The concept extractor 140 applies the corresponding retrieved resources from the NLP resources 144 to the electronic medical report document 130. The application of the retrieved resources with the other NLP logic 142 analysis, which may comprise any known or later developed NLP operations, identifies concepts present within the electronic medical report document 130 that match or are otherwise semantically related to the key terms, phrases, concepts, and other descriptors identified in the retrieved resources. For example, as shown in FIG. 1, the electronic medical report document 130 comprises text describing a corresponding medical image 120, where the text, in this example, comprises:

Stable cardiomediastinal silhouette with mild cardiomegaly and aortic ectasia and tortuosity. No alveolar consolidation, no findings of pleural effusion. Chronic appearing bilateral rib contour deformities compatible with old fractures. No pneumothorax.

From this text, the concept extractor 140, using NLP logic 142 and corresponding resources retrieved from the NLP resources 144, a listing of concepts 150 present in the electronic medical record document 130 is generated as follows:

1. Cardiomegaly/mild aorta/tortuous deformity/ribs/bilateral/chronic fractures; and
2. Bone/ribs/bilateral/multiple/healed.

The concepts found in the electronic medical report document 130 by the concept extractor 140 are input to a vector embedding engine 170 which converts the concepts to a vector representation through a vector embedding, sometimes also referred to as word embedding, approach. That is, concepts, terms, phrases, and other descriptors found through concept extraction by the concept extractor 140 are matched to vector slots in a vector representation whose values are then set according to the occurrence of such corresponding concepts, terms, phrases, and other descriptors in the concept extraction results 150. For example, the vector embedding engine 170 may be configured to recognize a set of concepts, which again may be specific to the particular domain, imaging technology, modality, and other medical imaging characteristics. Each concept in this set of concepts may have a corresponding vector slot in the vector representation. If the results 150 contain elements that correspond to that concept, then the numerical value in the vector slot is set to a corresponding value indicating the presence of that concept in the results 150, e.g., the value may be changed from a 0 value indicating that the concept is not present, to a 1 value indicating that the concept is present. In some embodiments, the numerical value in the vector slot may be a counter that counts a number of occurrences of the concept in the electronic medical report document 130.

The vector representation output by the vector embedding engine 170 is input to a long short-term memory (LSTM) network 180 which processes semantic and relational information in sentences of the electronic medical record document 130. That is, the vector embedding engine 170 converts the existence of concepts in the medical report 130 into a vector of values for the concepts. This vector is then input to the LSTM network 180 which converts the vector to a more sophisticated network that models language, and the relationship between concepts, rather than just their existence and frequency.

At approximately a same time, such as part of a parallel operation to the processing of the electronic medical report document 130, the medical image data 120 is input to a medical image processing convolutional neural network (CNN) 160. The CNN 160 generates numerical values that are a descriptor of the features of the medical image data 120 identified by the nodes of the CNN 160. The use of a CNN 160 to analyze a medical image 120 to generate a vector representation of the medical image is generally known in the art and thus, a more detailed explanation is not provided herein. An example of a CNN that is used analyze a medical image is described in Moradi et al., "A Hybrid Learning Approach for Semantic Labeling of Cardiac CT Slices and Recognition of Body Position," 2016 IEEE 13$^{th}$ International Symposium on Biomedical Imaging (ISBI), pp. 1418-1421, Apr. 13-16, 2016.

The CNN 160 outputs a vector representation of the features in the medical image data 120, which is concatenated with the vector representation of the concepts found in the associated electronic medical report 130 output by the LSTM network 180. The output of the fully connected layer from the CNN 160 is used for image representation and the concatenation of this feature vector from the CNN 160 and the vector output from the LSTM 180 gives the full vector input that that is provided to the multi-layer perceptron (MLP) 190. It should be noted that the vector outputs for the CNN 160 and LSTM 180 may not be binary, e.g., the only binary vector may be the vector output from the vector embedding unit 170 which is processed by LSTM 180 into a non-binary vector output. The role of the MLP 190 is to learn from this concatenated vector input, where the medical image features related to the textual concepts lie in the medical image 120.

Thus, the concatenated vector is input to the MLP 190 which is a machine learning model that operates on the concatenated vector representation to generate coordinate values 195 for coordinates of a bounding region of the medical image data 120 where an anomaly is reported in the associated electronic medical report document 130. That is, the input to the MLP 190 is a numeric representation of the medical image 120 (i.e. the extracted features of the medical image 120) and a numeric representation of the concepts of interest in the medical report 130 associated with the medical image 120. The output of the MLP 190 is a indication of where those concepts show up in the medical image in the form of coordinates. The MLP 190 is trained using enough training medical images and corresponding medical reports, where these coordinates are marked for the training images, such that the MLP 190 learns that the location of a concept specified in the medical report is at a particular set of coordinates within the medical image, e.g., the concept of "cardiomegaly" is in the anatomical structure of the heart in the medical image.

The coordinate values 195 output by the MLP 190 may be used to annotate the original medical image data 120 to include a bounding region, e.g., a bounding polygon, indicating a segment of the medical image where an anomaly was reported in the electronic medical report 130. Thus, modified medical image data, i.e. an annotated medical image, 199 may be generated or metadata may be added to the original medical image data 120 to specify the coordinates of the bounding region for use when the medical image is rendered in a medical image viewer application or provided to a cognitive system for performance of cognitive operations.

Figure 2A:
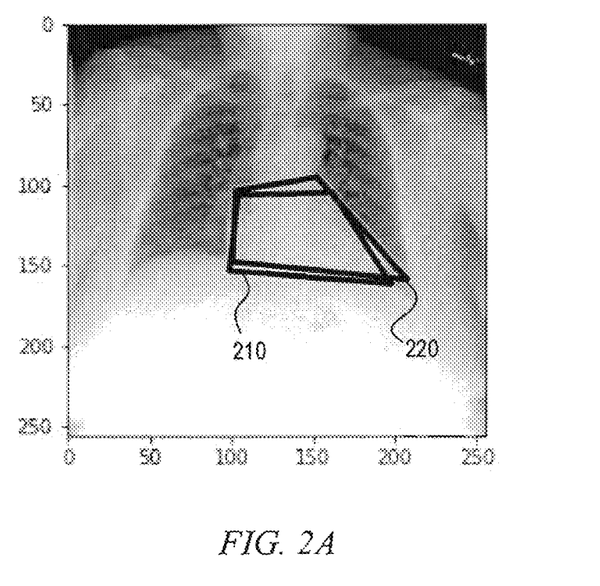
FIGS. 2A and 2B are example diagrams of medical images with bounding regions identified via automated contour annotation in accordance with one illustrative embodiment.
Figure 2B:
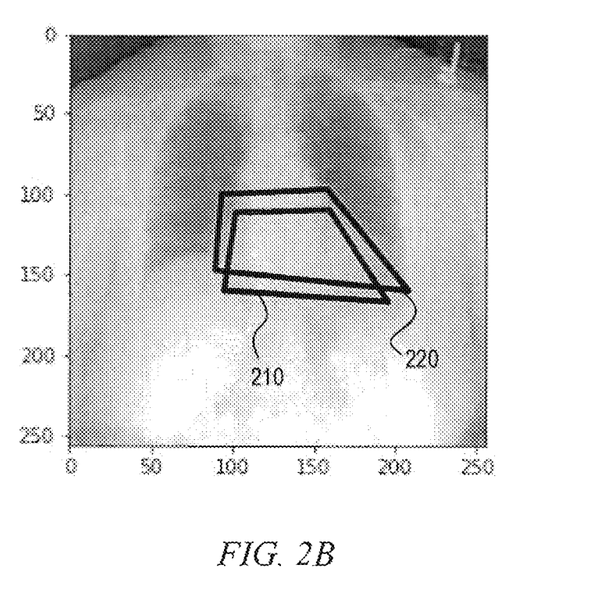

FIGS. 2A and 2B are example diagrams of medical images with bounding regions identified via automated contour annotation in accordance with one illustrative embodiment. In each of FIGS. 2A and 2B, chest X-ray images are shown in which there is a first bounding polygon 210 corresponding to a manually specified contour that is manually generated by a SME, such as a radiologist or other domain expert. The second bounding polygon 220 corresponds to a contour identified through operation of the mechanisms of the illustrative embodiments. It can be seen from the representations in FIGS. 2A and 2B that the polygons 210 and 220, while not exactly aligned, are relatively close in proximity to each other within the medical image. Thus, the automated contour annotation mechanism of the illustrative embodiments provides accurate results for performing automatic annotation of contours corresponding to anomalous regions of medical images based on processing of corresponding electronic medical record documents.

It should be appreciated that MLP network 190 may be trained during a training phase of operation whereby the medical image data 120 may be annotated medical image data that specifies the correct regions of the medical image where anomalies are present such that relationships between the concepts present in the corresponding electronic medical report document 130 and the particular coordinates of the correct anomalous region are learned by the MLP network 190. Thus, a training data set may be input that comprises the annotated training medical image data 120 and corresponding electronic medical report document 130 which is then processed via the CNN 160 and concept extractor 140, vector embedding logic 170, and LSTM network 180, to generate the vector representations of the medical image data 120 and the concepts found in the electronic medical report document 130 which are then concatenated as noted above. The concatenated vector is then input to the MLP 190 which outputs its determination of coordinates 195 for the anomalous region.

Training logic (not shown) may be employed to compare the coordinates 195 generated by the MLP 190 to the ground truth specified by the annotations of the training medical image data 120. A degree of correspondence, or difference, is determined and appropriate modifications of weights to nodes in the MLP 190 may be applied to the MLP 190 to modify its operation, such as via a machine learning approach. The modifications of the weights are made so as to minimize the difference between the MLP 190 output of coordinates 195 and the ground truth of the annotations in the training medical image data 120. This process may be repeated for various training medical image data 120 until the MLP 190 operation converges, e.g., an amount of improvement in the difference between the output 195 and the ground truth is equal to or below a threshold value. At this point, the MLP 190 is fully trained and ready for deployment for processing new medical image data and corresponding electronic medical report documents.

When trained, the mechanisms of the illustrative embodiments may be utilized to annotate other medical image data, such as may be provided by other medical image data sources, provided in a corpus or corpora of medical image data, or the like. Such operations may be performed in response to requests from users to perform such analysis and annotation of medical image data. For example, a referring physician, may be engaged in reviewing the medical images taken for a patient. The medical imaging service provider may provide the medical image data and the corresponding electronic medical report document to the doctor, but the medical image data may not be annotated with what is described in the medical report. The doctor, while a medical professional, may not have the same level of training and expertise as a radiologist, sonographer, MM expert, or the like, and thus, may not readily identify the anomalies mentioned in the medical report in the corresponding medical images. As a result, the doctor may request that the mechanisms of the illustrative embodiments perform automated contour annotation of the medical image to assist the doctor in treating the patient.

In other illustrative embodiments, the mechanisms of the illustrative embodiments may be used to expand a set of annotated medical image data that may be used for training other cognitive systems or medical image analysis systems. That is, as noted above, annotated training medical image data may be utilized to assist with the training of the MLP 190 of the illustrative embodiments. Similarly, other cognitive systems and medical image analysis systems may utilize training medical image data having annotations that provide a ground truth or basis for the training. The mechanisms of the illustrative embodiments, by providing automated contour annotation of medical images effectively can be used to expand a relatively small manually annotated set of training medical images by including additional automatically annotated medical images. Thus, the automatically annotated medical images generated by the mechanisms of the illustrative embodiments may be added to a previously existing annotated medical image dataset to expand that annotated medical image dataset, which may then be used as input for training a cognitive system or other medical image analysis system.

Figure 3:
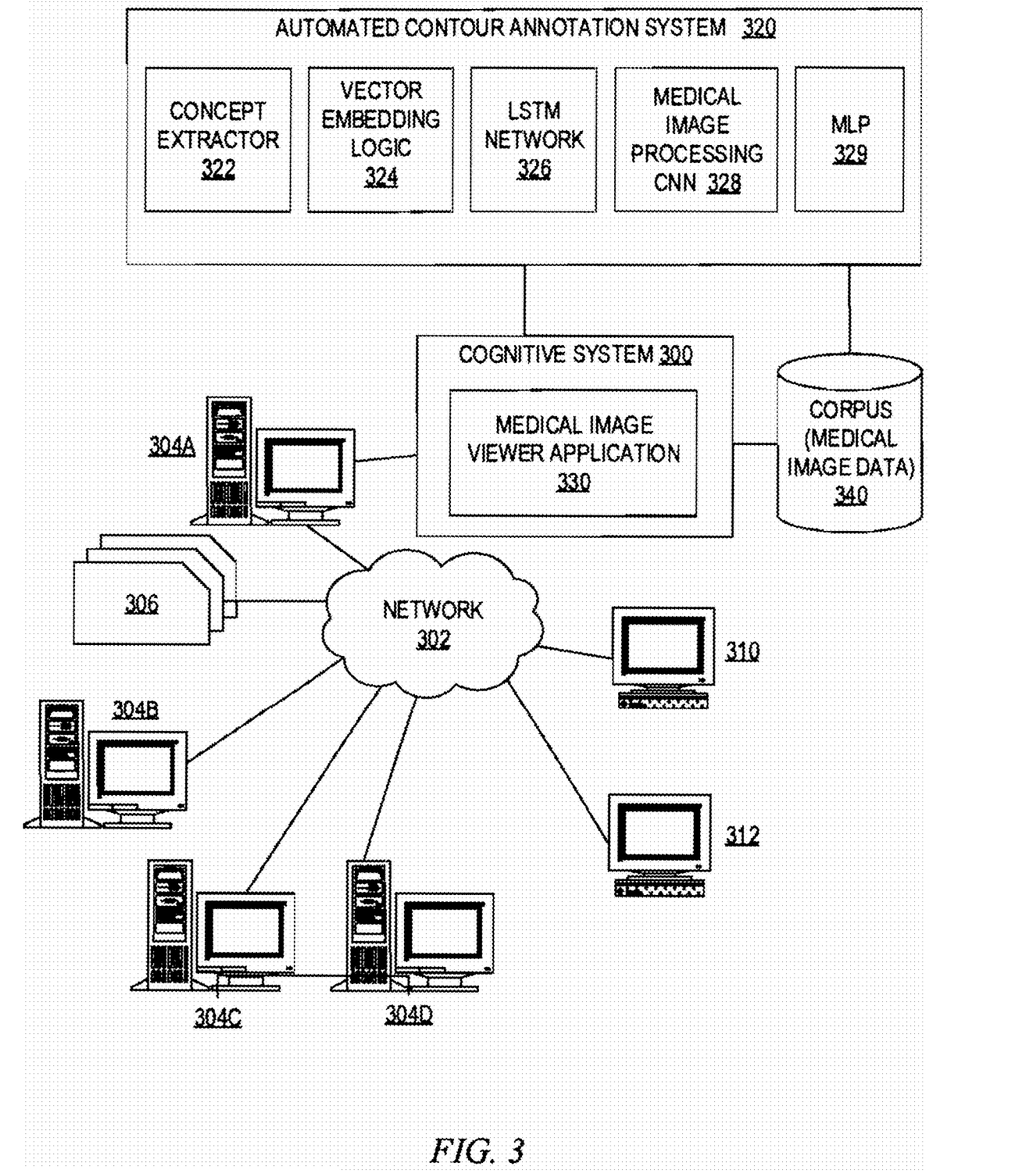
FIG. 3 depicts a schematic diagram of one illustrative embodiment of a cognitive healthcare system in a computer network.

FIG. 3 depicts a schematic diagram of one illustrative embodiment of a cognitive system 300 implementing a medical image viewer application 330 in a computer network 302. The cognitive system 300 is implemented on one or more computing devices 304A-D (comprising one or more processors and one or more memories, and potentially any other computing device elements generally known in the art including buses, storage devices, communication interfaces, and the like) connected to the computer network 302. For purposes of illustration only, FIG. 3 depicts the cognitive system 300 being implemented on computing device 304A only, but as noted above the cognitive system 300 may be distributed across multiple computing devices, such as a plurality of computing devices 304A-D. The network 302 includes multiple computing devices 304A-D, which may operate as server computing devices, and 310-712 which may operate as client computing devices, in communication with each other and with other devices or components via one or more wired and/or wireless data communication links, where each communication link comprises one or more of wires, routers, switches, transmitters, receivers, or the like.

In some illustrative embodiments, the cognitive system 300 and network 302 enables question processing and answer generation (QA) functionality for one or more cognitive system users via their respective computing devices 310-312. In other embodiments, the cognitive system 300 and network 302 may provide other types of cognitive operations including, but not limited to, request processing and cognitive response generation which may take many different forms depending upon the desired implementation, e.g., cognitive information retrieval, training/instruction of users, cognitive evaluation of data, such as medical imaging data, or the like. Other embodiments of the cognitive system 300 may be used with components, systems, sub-systems, and/or devices other than those that are depicted herein.

In some illustrative embodiments, the client computing devices 310 and 312 may be used as a mechanism for logging onto or otherwise accessing the cognitive system 300 for purposes of viewing medical imaging studies for patients and perform operations for classifying and/or corroborating automated classification of such medical imaging studies. For example, a doctor or other medical professional may utilize a client computing device 310 to access the services and functionality provided by the cognitive system 300 and the medical image viewer application 330 to view medical images of one or more medical imaging studies stored in the corpus 340 for one or more patients. The user of the client computing device 310 may view the medical images and perform operations for annotating the medical images, adding notes to patient electronic medical records (EMRs), and any of a plethora of other operations that may be performed through human-computer interaction based on the human's viewing of the medical images via the cognitive system 300.

In some illustrative embodiments, the cognitive system 300 may be configured to implement a request processing pipeline that receive inputs from various sources. The requests may be posed in the form of a natural language question, natural language request for information, natural language request for the performance of a cognitive operation, or the like. For example, the cognitive system 300 may receive input from the network 302, a corpus or corpora of electronic documents 306, cognitive system users, and/or other data and other possible sources of input. In one embodiment, some or all of the inputs to the cognitive system 300 are routed through the network 302. The various computing devices 304A-D on the network 302 include access points for content creators and cognitive system users. Some of the computing devices 304A-D include devices for a database storing the corpus or corpora of data 306 (which is shown as a separate entity in FIG. 3 for illustrative purposes only). Portions of the corpus or corpora of data 306 may also be provided on one or more other network attached storage devices, in one or more databases, or other computing devices not explicitly shown in FIG. 3. The network 302 includes local network connections and remote connections in various embodiments, such that the cognitive system 300 may operate in environments of any size, including local and global, e.g., the Internet.

The request processing pipeline of the cognitive system 300 may comprises a plurality of stages for processing an input question/request based on information obtained from the corpus or corpora of data 306 and/or 340. For example, a doctor may input a question of the type "Where is the anomaly in Patient A's chest X-ray?" or may input a request of the type "Identify the anomaly in Patient A's chest X-ray." Alternatively, the question/request may be the selection, via a user interface of the like, of a particular operation to be performed by the cognitive system on a particular viewed medical image, such as may be viewed via the medical image viewer application 330. For example, the doctor may access a medical image associated with a patient and select an option to identify any anomalous regions in the medical image.

The pipeline generates answers/responses for the input question or request based on the processing of the input question/request and the corpus or corpora of data 306, 340. For example, the request to render the medical image, or to identify an anomalous region in the medical image, may invoke the operation of the automated contour annotation system 320 of the illustrative embodiments. Alternatively, the operation of the automated contour annotation system 320 of the illustrative embodiments may be performed in response to new medical imaging data and corresponding electronic medical report documents being received, e.g., added to the corpus 340 and/or 306. In the latter case, the cognitive system 300 may perform a retrieval operation from the corpus 340 of the already automatically annotated medical image data for performance of cognitive operations and/or rendering of the medical images via the medical image viewer application 330 with anomalous regions being depicted in accordance with the automatic contour annotations generated by the illustrative embodiments.

In some illustrative embodiments, the cognitive system 300 may be the IBM Watson™ cognitive system available from International Business Machines Corporation of Armonk, N.Y., which is augmented with the mechanisms of the illustrative embodiments described herein. More information about the pipeline of the IBM Watson™ cognitive system may be obtained, for example, from the IBM Corporation website, IBM Redbooks, as well as in Yuan et al., "Watson and Healthcare," IBM developerWorks, 2011 and "The Era of Cognitive Systems: An Inside Look at IBM Watson and How it Works" by Rob High, IBM Redbooks, 2012.

As shown in FIG. 3, the cognitive system 300 may operate in conjunction with an automated contour annotation system 320, in accordance with the mechanisms of the illustrative embodiments. The automated contour annotation system 320, and its various components 322-329, may be implemented in specialized hardware, software executed on hardware, or any combination of specialized hardware and software executed on hardware. The automated contour annotation system 320 comprises a concept extractor 322, vector embedding logic 324, LSTM network 326, medical image processing convolutional neural network (CNN) 328, and multi-layer perceptron (MLP) 329.

The MLP 329 is preferably specifically configured and trained in the manner previous described above with regard to one or more of the illustrative embodiments, so as to identify relationships between medical image features extracted by the CNN 328 and concepts identified by the LSTM network 326 based on NLP operations performed by the concept extractor 322 and vector representation generated using the vector embedding logic 324. The MLP 329 is further configured and trained to correlate these relationships with coordinates in a medical image for points along a contour, or bounding region, that identify areas where an anomaly is identified and documented in the electronic medical report document associated with the medical image data that is input.

The automated contour annotation system 320 operates in the manner previously described above with reference to FIG. 1, where similarly named elements perform similar operations. Thus, for example, a doctor or other medical professional operating a client computing device 310 may log onto the cognitive system 300 and access a medical imaging study associated with a patient, such as from corpus 340, for example. The medical imaging study may be generated by a medical imaging service provider using medical imaging equipment and may provide the medical imaging study data, comprising a plurality of medical images in a digital form, for storage in the corpus 340. The medical imaging study data and/or individual medical images, may have associated medical reports that are provided in an electronic form as well and may likewise be stored in the corpus 340 in association with the medical imaging study or medical image data.

The medical professional may submit a request to the cognitive system 300, such as via a graphical user interface (GUI) of the medical image viewer application 330, or the like, to view a medical image and have the cognitive system 300 identify anomalous regions within the medical image. Responsive to the request, the cognitive system 300, in processing the request via the request processing pipeline, may invoke the automated contour annotation system 320, which has already been trained as discussed above, to automatically annotate contours within the medical image defining anomalous regions. The automated contour annotation system 320 may process the medical image data retrieved from the corpus 340, as well as the electronic medical report document associated with the medical image data, in the manner previously described above with regard to FIG. 1, to thereby automatically identify contour points defining an anomalous region in the medical image data. The contour points may then be used to graphically render a bounding polygon or other contour indicating the anomalous region on a rendering of the medical image via the medical image viewer application 330. Moreover, the medical image data may be modified and updated to include metadata specifying the automatically identified and annotated contour in the medical image.

As mentioned above, in an alternative embodiment, the operations of the automated contour annotation system 320 may be automatically invoked when new medical image data and medical report data are added to the corpus 340. For example, as a pre-processing operation when the data is added to the corpus 340, the automated contour annotation system 320 may operate on the data to identify the coordinates of the anomalous regions in the medical images and annotate them, thereby updating the medical image data to include metadata specifying the anomalous region(s). Thereafter, during runtime when the medical professional requests identification of anomalous regions in the medical image, the annotated medical image may be retrieved from the corpus 340 without having to then invoke the operations of the automated contour annotation system 320.

Thus, the illustrative embodiments provide mechanisms for automatically annotating medical images with contours defining anomalous regions in the medical images. This greatly reduces the amount of human effort and resources required to generate annotated medical images which can be used during runtime operation and/or training of cognitive systems and medical image analysis systems. The illustrative embodiments leverage the information that may be extracted from the medical reports associated with the medical images to annotate the non-annotated medical images by utilizing a trained machine learning system that learns the association of concepts in medical reports with features in medical images and coordinates of anomalous regions in medical images.

Figure 4:
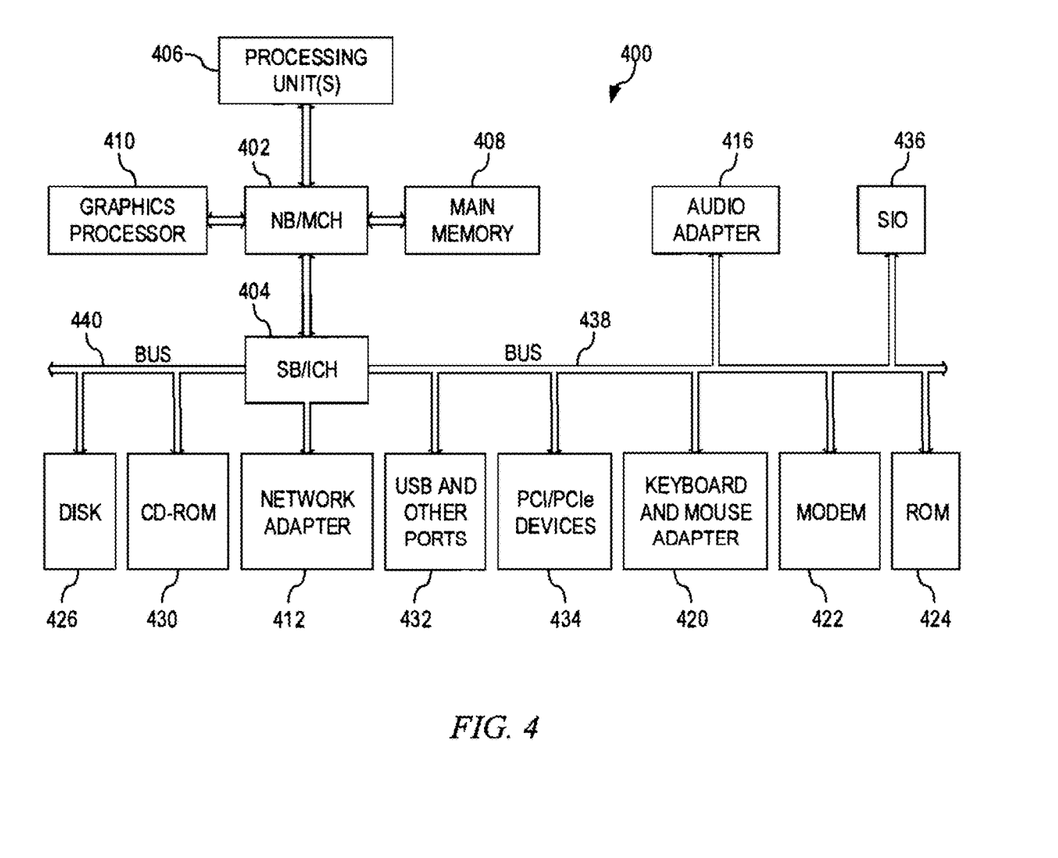
FIG. 4 is a block diagram of an example data processing system in which aspects of the illustrative embodiments are implemented.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 4 is provided as an example of one type of data processing system in which aspects of the present invention may be implemented. Many other types of data processing systems may be likewise configured to specifically implement the mechanisms of the illustrative embodiments.

FIG. 4 is a block diagram of an example data processing system in which aspects of the illustrative embodiments are implemented. Data processing system 400 is an example of a computer, such as a server 304A-D or client 310-712 in FIG. 3, in which computer usable code or instructions implementing the processes for illustrative embodiments of the present invention are located. In one illustrative embodiment, FIG. 4 represents a server computing device, such as a server 304A, which, which implements a cognitive system 300 and medical image viewer application 330, where the server 304A further is specifically configured and executes hardware and/or software logic to implement the semi-supervised GAN classification system 320 of FIG. 3.

In the depicted example, data processing system 400 employs a hub architecture including North Bridge and Memory Controller Hub (NB/MCH) 402 and South Bridge and Input/Output (I/O) Controller Hub (SB/ICH) 404. Processing unit 406, main memory 408, and graphics processor 410 are connected to NB/MCH 402. Graphics processor 410 is connected to NB/MCH 402 through an accelerated graphics port (AGP).

In the depicted example, local area network (LAN) adapter 412 connects to SB/ICH 404. Audio adapter 416, keyboard and mouse adapter 420, modem 422, read only memory (ROM) 424, hard disk drive (HDD) 426, CD-ROM drive 430, universal serial bus (USB) ports and other communication ports 432, and PCI/PCIe devices 434 connect to SB/ICH 404 through bus 438 and bus 440. PCI/PCIe devices may include, for example, Ethernet adapters, add-in cards, and PC cards for notebook computers. PCI uses a card bus controller, while PCIe does not. ROM 424 may be, for example, a flash basic input/output system (BIOS).

HDD 426 and CD-ROM drive 430 connect to SB/ICH 404 through bus 440. HDD 426 and CD-ROM drive 430 may use, for example, an integrated drive electronics (IDE) or serial advanced technology attachment (SATA) interface. Super I/O (SIO) device 436 is connected to SB/ICH 404.

An operating system runs on processing unit 406. The operating system coordinates and provides control of various components within the data processing system 400 in FIG. 4. As a client, the operating system is a commercially available operating system such as Microsoft® Windows 10®. An object-oriented programming system, such as the Java™ programming system, may run in conjunction with the operating system and provides calls to the operating system from Java programs or applications executing on data processing system 400.

As a server, data processing system 400 may be, for example, an IBM® eServer™ System p® computer system, running the Advanced Interactive Executive (AIX®) operating system or the LINTJX® operating system. Data processing system 400 may be a symmetric multiprocessor (SMP) system including a plurality of processors in processing unit 406. Alternatively, a single processor system may be employed.

Instructions for the operating system, the object-oriented programming system, and applications or programs are located on storage devices, such as HDD 426, and are loaded into main memory 408 for execution by processing unit 406. The processes for illustrative embodiments of the present invention are performed by processing unit 406 using computer usable program code, which is located in a memory such as, for example, main memory 408, ROM 424, or in one or more peripheral devices 426 and 430, for example.

A bus system, such as bus 438 or bus 440 as shown in FIG. 4, is comprised of one or more buses. Of course, the bus system may be implemented using any type of communication fabric or architecture that provides for a transfer of data between different components or devices attached to the fabric or architecture. A communication unit, such as modem 422 or network adapter 412 of FIG. 4, includes one or more devices used to transmit and receive data. A memory may be, for example, main memory 408, ROM 424, or a cache such as found in NB/MCH 402 in FIG. 4.

Those of ordinary skill in the art will appreciate that the hardware depicted in FIGS. 3 and 4 may vary depending on the implementation. Other internal hardware or peripheral devices, such as flash memory, equivalent non-volatile memory, or optical disk drives and the like, may be used in addition to or in place of the hardware depicted in FIGS. 3 and 4. Also, the processes of the illustrative embodiments may be applied to a multiprocessor data processing system, other than the SMP system mentioned previously, without departing from the spirit and scope of the present invention.

Moreover, the data processing system 400 may take the form of any of a number of different data processing systems including client computing devices, server computing devices, a tablet computer, laptop computer, telephone or other communication device, a personal digital assistant (PDA), or the like. In some illustrative examples, data processing system 400 may be a portable computing device that is configured with flash memory to provide non-volatile memory for storing operating system files and/or user-generated data, for example. Essentially, data processing system 400 may be any known or later developed data processing system without architectural limitation.

Figure 5:
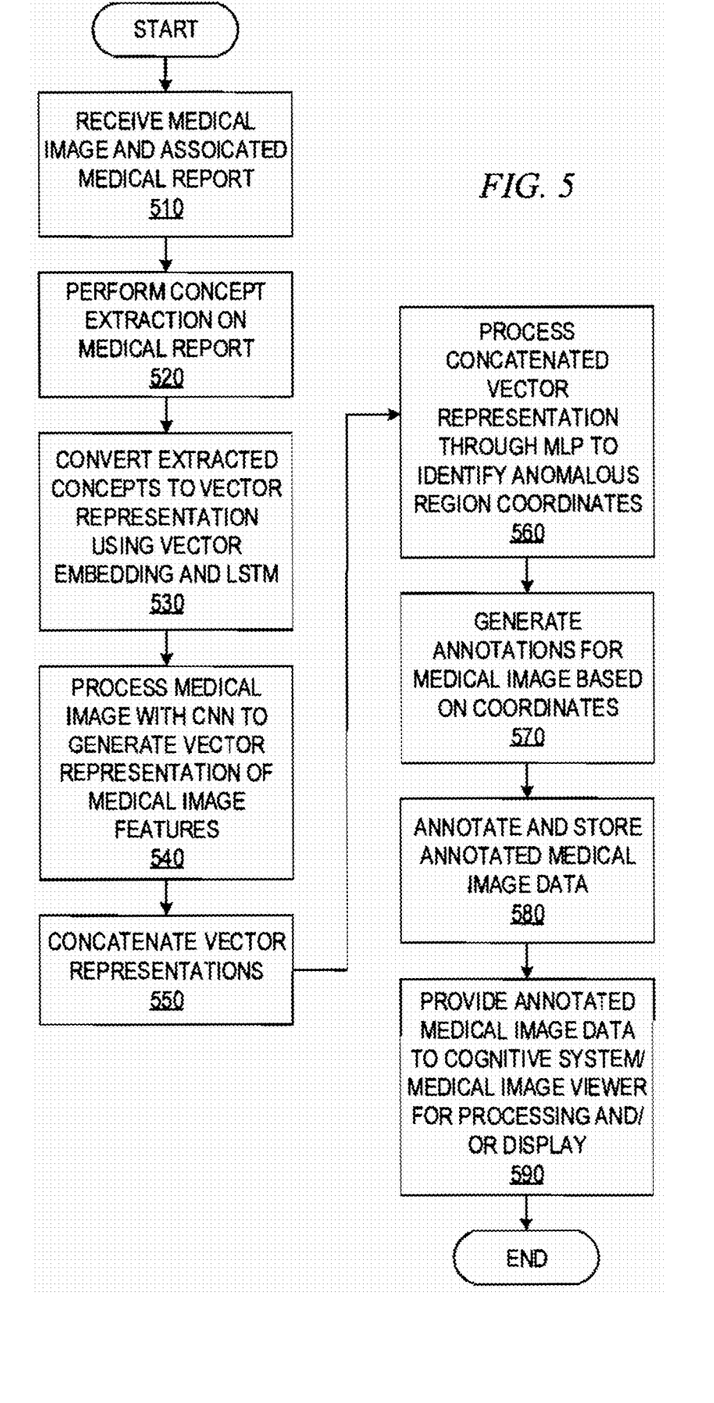
FIG. 5 is a flowchart outlining an example operation for performing automatic contour annotation in accordance with one illustrative embodiment.

FIG. 5 is a flowchart outlining an example operation for performing automatic contour annotation in accordance with one illustrative embodiment. As shown in FIG. 5, the operation starts by receiving a medical image and associated medical report, where the medical image and associated medical report are electronically provided as data structures via one or more computing devices (step 510). Concept extraction is performed on the medical report using natural language processing techniques and natural language processing resources, which may be domain specific and/or specific to the particular imaging technology used to generate the medical image (step 520). The extracted concepts found through the concept extraction are then converted to a vector representation using vector embedding and an LSTM (step 530).

Meanwhile, the medical image is processed using a CNN to generate a vector representation of the medical image features (step 540). It should be appreciated that while the flowchart shows step 540 occurring after steps 520-530, this is not intended to require a sequential performance of these operations. To the contrary, these operations may be performed in parallel.

The vector representations generated based on the concept extraction and the medical image feature extraction are then concatenated to generate a concatenated vector representation (step 550). The concatenated vector is then processed through a MLP to identify anomalous region coordinates in the medical image (step 560). Based on the identification of the anomalous region coordinates, corresponding annotations for the medical image are generated (step 570) and the medical image is annotated and stored (step 580). The annotated medical image data may then be provided to a cognitive system for performance of cognitive operations, a medical image viewer application for viewing of the medical image and corresponding anomalous regions, or to another medical image analysis system for performance of medical image analysis based on the automatic identification and annotation of contours of anomalous regions in the medical image data (step 590). The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, wherein the at least one memory comprises instructions that are executed by the at least one processor to cause the at least one processor to implement a neural network, a concept extractor, and a machine learning model, and wherein the method comprises:
   processing, by the neural network of the data processing system, a medical image to extract image features of the medical image;
   processing, by the concept extractor of the data processing system, a portion of text associated with the medical image to extract concepts associated with the portion of text;
   correlating, by the machine learning model of the data processing system, the extracted image features with the extracted concepts; and
   automatically generating, by the data processing system, an annotated medical image based on the correlation of the extracted image features and extracted concepts, wherein an annotation of the annotated medical image specifies a region of interest corresponding to both an extracted image feature and an extracted concept, thereby automatically mapping the portion of text to a relevant region of the medical image.

2. The method of claim 1, further comprising:
   training at least one of a cognitive system, machine learning system, or convolutional neural network to perform medical image classification based on the generated annotated medical image.

3. The method of claim 1, wherein processing the portion of text associated with the medical image comprises executing natural language processing logic, specifically configured for analysis of text with regard to medical imaging concepts, on the portion of text to extract at least one of key terms, phrases, or descriptors from the portion of text corresponding to medical imaging concepts.

4. The method of claim 3, wherein the natural language processing logic is specifically configured for at least one of a particular domain of medical images being analyzed, a specific medical imaging technology being utilized to capture medical images, a particular modality for capturing medical images, or a specific anatomical region of a patient.

5. The method of claim 1, wherein processing the portion of text associated with the medical image to extract concepts associated with the portion of text comprises:
  extracting one or more natural language content elements referencing features of the medical image;
  embedding the one or more natural language content elements into a vector representation; and
  inputting the vector representation into a long short-term memory (LSTM) network that processes semantic and relational information in the portion of text.

6. The method of claim 5, wherein correlating, by the machine learning model of the data processing system, the extracted image features with the extracted concepts comprises:
  inputting a first output of the LSTM network and a second output of the neural network specifying the extracted image features to a multi-layer perceptron; and
  processing, by the multi-layer perceptron the first output and second output to generate a third output representing a series of points of a contour in the medical image.

7. The method of claim 6, wherein the contour in the medical image is a bounding area in the medical image where one or more abnormalities, referenced in the portion of text, are present.

8. The method of claim 1, wherein the portion of text is a medical imaging report generated by a subject matter expert in response to viewing the medical image.

9. The method of claim 1, wherein correlating, by the machine learning model of the data processing system, the extracted image features with the extracted concepts comprises generating a set of coordinates of vertices of a bounding polygon in the medical image where a concept in the extracted concepts is represented in the medical image.

10. The method of claim 1, wherein the processing of the medical image and the processing of the portion of text are performed in parallel to one another.

11. A computer program product comprising a computer readable storage medium having a computer readable program stored therein, wherein the computer readable program, when executed on a data processing system, causes the data processing system to implement a neural network, a concept extractor, and a machine learning model, and wherein the computer readable program further causes the data processing system to:
  process, by the neural network of the data processing system, a medical image to extract image features of the medical image;
  process, by the concept extractor of the data processing system, a portion of text associated with the medical image to extract concepts associated with the portion of text;
  correlate, by the machine learning model of the data processing system, the extracted image features with the extracted concepts; and
  automatically generate, by the data processing system, an annotated medical image based on the correlation of the extracted image features and extracted concepts, wherein an annotation of the annotated medical image specifies a region of interest corresponding to both an extracted image feature and an extracted concept, thereby automatically mapping the portion of text to a relevant region of the medical image.

12. The computer program product of claim 11, wherein the computer readable program further causes the data processing system to:
  train at least one of a cognitive system, machine learning system, or convolutional neural network to perform medical image classification based on the generated annotated medical image.

13. The computer program product of claim 11, wherein the computer readable program further causes the data processing system to process the portion of text associated with the medical image at least by executing natural language processing logic, specifically configured for analysis of text with regard to medical imaging concepts, on the portion of text to extract at least one of key terms, phrases, or descriptors from the portion of text corresponding to medical imaging concepts.

14. The computer program product of claim 13, wherein the natural language processing logic is specifically configured for at least one of a particular domain of medical images being analyzed, a specific medical imaging technology being utilized to capture medical images, a particular modality for capturing medical images, or a specific anatomical region of a patient.

15. The computer program product of claim 11, wherein the computer readable program further causes the data processing system to process the portion of text associated with the medical image to extract concepts associated with the portion of text at least by:
  extracting one or more natural language content elements referencing features of the medical image;
  embedding the one or more natural language content elements into a vector representation; and
  inputting the vector representation into a long short-term memory (LSTM) network that processes semantic and relational information in the portion of text.

16. The computer program product of claim 15, wherein the computer readable program further causes the data processing system to correlate, by the machine learning model of the data processing system, the extracted image features with the extracted concepts at least by:
  inputting a first output of the LSTM network and a second output of the neural network specifying the extracted image features to a multi-layer perceptron; and
  processing, by the multi-layer perceptron the first output and second output to generate a third output representing a series of points of a contour in the medical image.

17. The computer program product of claim 16, wherein the contour in the medical image is a bounding area in the medical image where one or more abnormalities, referenced in the portion of text, are present.

18. The computer program product of claim 11, wherein the portion of text is a medical imaging report generated by a subject matter expert in response to viewing the medical image.

19. The computer program product of claim 11, wherein the computer readable program further causes the data processing system to correlate, by the machine learning model of the data processing system, the extracted image features with the extracted concepts at least by generating a set of coordinates of vertices of a bounding polygon in the medical image where a concept in the extracted concepts is represented in the medical image.

20. An data processing system comprising:
  at least one processor; and
  at least one memory coupled to the at least one processor, wherein the at least one memory comprises instructions which, when executed by the at least one processor, cause the at least one processor to implement a neural network, a concept extractor, and a machine learning model, and wherein the instructions further cause the at least one processor to:

process, by the neural network of the data processing system, a medical image to extract image features of the medical image;

process, by the concept extractor of the data processing system, a portion of text associated with the medical image to extract concepts associated with the portion of text;

correlate, by the machine learning model of the data processing system, the extracted image features with the extracted concepts; and automatically generate an annotated medical image based on the correlation of the extracted image features and extracted concepts, wherein an annotation of the annotated medical image specifies a region of interest corresponding to both an extracted image feature and an extracted concept, thereby automatically mapping the portion of text to a relevant region of the medical image.

* * * * *